(12) United States Patent
Beese et al.

(10) Patent No.: US 8,522,996 B2
(45) Date of Patent: Sep. 3, 2013

(54) DISPOSABLE BIOREACTOR, KIT FOR THE SAME AND METHOD FOR ITS PRODUCTION

(75) Inventors: Jochen Beese, Norderstedt (DE); Sven Eikelmann, Hamburg (DE)

(73) Assignee: Eppendorf AG (DE)

( * ) Notice: Subject to any disclaimer, the term of this patent is extended or adjusted under 35 U.S.C. 154(b) by 584 days.

(21) Appl. No.: 12/713,879

(22) Filed: Feb. 26, 2010

(65) Prior Publication Data

US 2010/0291674 A1 Nov. 18, 2010

Related U.S. Application Data

(60) Provisional application No. 61/177,389, filed on May 12, 2009.

(30) Foreign Application Priority Data

May 12, 2009 (EP) ..................................... 09006409

(51) Int. Cl.
*B65D 45/28* (2006.01)
*C12M 1/00* (2006.01)

(52) U.S. Cl.
USPC .................... 220/323; 435/304.1; 435/289.1; 435/302.1; 435/286.1; 220/260; 220/265; 220/326; 220/4.24; 220/786; 220/788; 220/315

(58) Field of Classification Search
USPC ..... 435/304.1, 289.1, 302.1, 286.1; 220/260, 220/265, 326, 4.24, 786, 788, 315, 323
See application file for complete search history.

(56) References Cited

U.S. PATENT DOCUMENTS

| | | | |
|---|---|---|---|
| 3,702,806 A | 11/1972 | Oliva | |
| 3,814,278 A | 6/1974 | Beierle | |
| 3,870,602 A | 3/1975 | Froman et al. | |
| 5,979,691 A | 11/1999 | Von Holdt | |
| 2005/0239198 A1 | 10/2005 | Kunas et al. | |
| 2005/0239199 A1 | 10/2005 | Kunas et al. | |
| 2006/0205065 A1 | 9/2006 | Bossi et al. | |
| 2009/0311776 A1 | 12/2009 | Kelly, Jr. et al. | |

FOREIGN PATENT DOCUMENTS

| | | |
|---|---|---|
| DE | 10 2006 022 651 | 10/2007 |
| WO | WO 94/19452 | 9/1994 |
| WO | WO 2007/134267 | 11/2007 |
| WO | WO 2009/009771 | 1/2009 |

*Primary Examiner* — Nathan Bowers
(74) *Attorney, Agent, or Firm* — Hiscock & Barclay, LLP

(57) ABSTRACT

The present invention discloses a disposable bioreactor, consisting of a container and a cap, which is connectable to the same and cannot be detached without destruction. For this purpose, the cap comprises a retaining structure with a plurality of locking arms running in the lateral direction, while the locking arms are adapted to be resiliently shortened in the longitudinal direction and to be locked vertically to the longitudinal direction in the container by way of a retaining surface.

12 Claims, 8 Drawing Sheets

Figure 1:
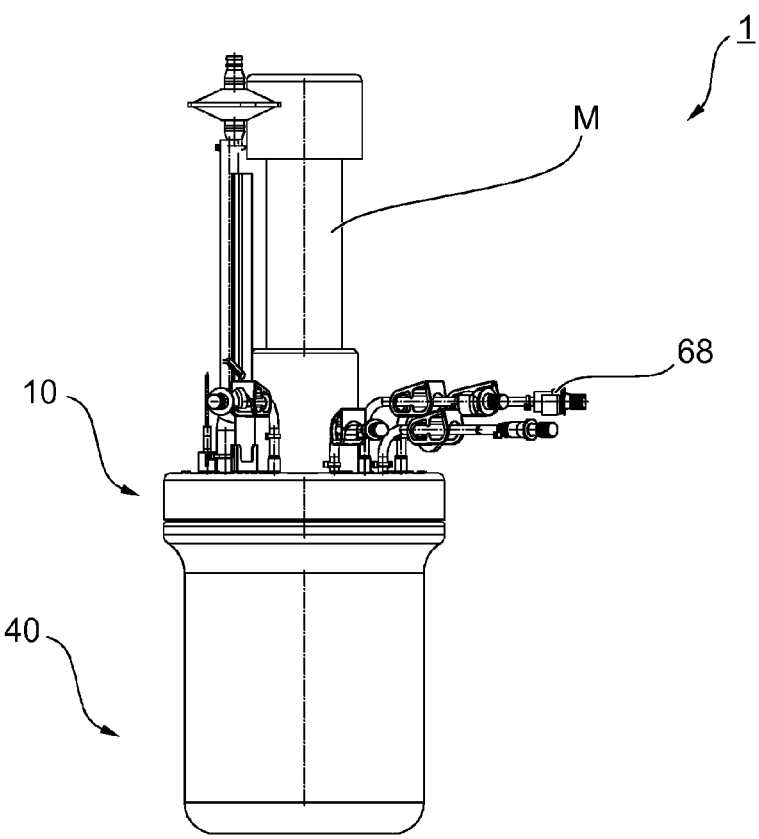

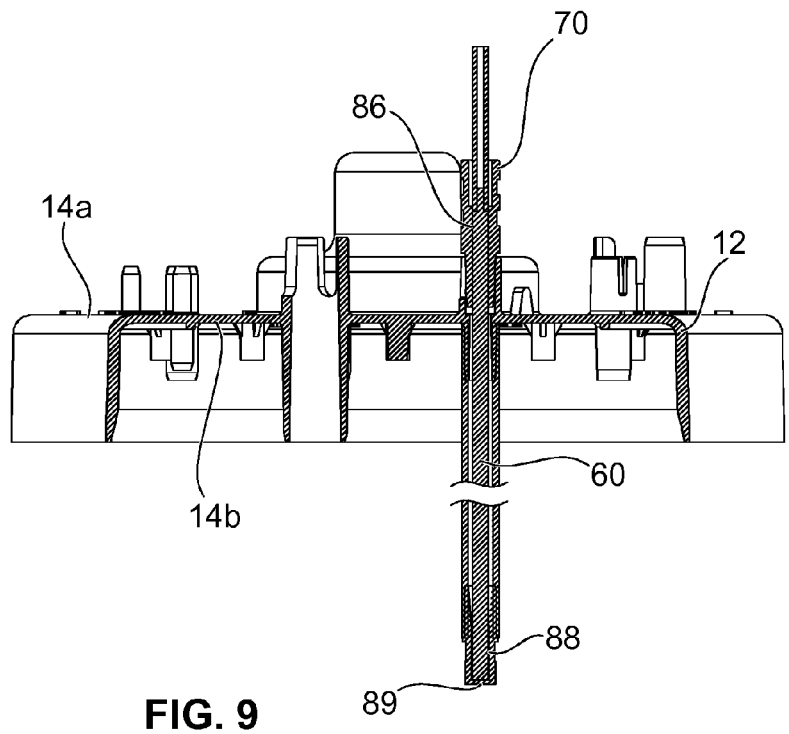
FIG. 9
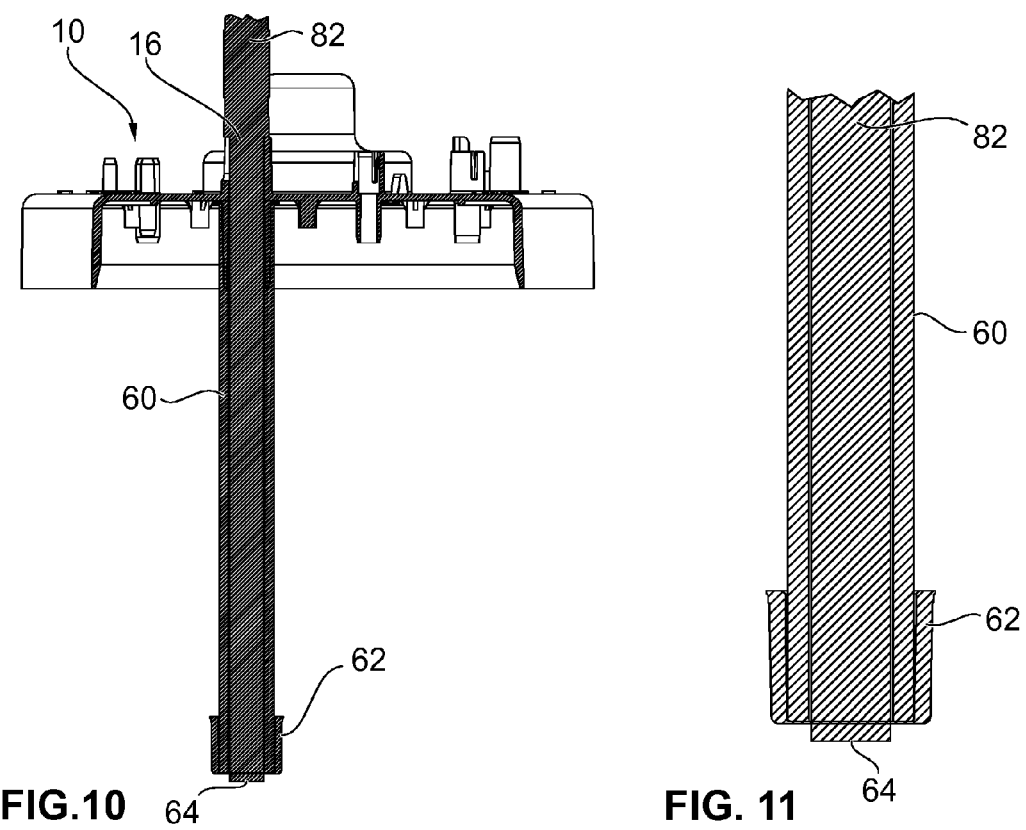
FIG. 10
FIG. 11

DISPOSABLE BIOREACTOR, KIT FOR THE SAME AND METHOD FOR ITS PRODUCTION

CROSS REFERENCE TO RELATED APPLICATION

This patent application claims priority of requisite sections under 35 USC §119 to provisional patent application, U.S. Ser. No. 61/177,309, filed May 12, 2009 and EP Application No. 09006409.8, filed May 12, 2009, each application herein incorporated by reference in its entirety.

FIELD OF THE INVENTION

The present invention is related to a disposable bioreactor which is composed of a body having rigid walls. In particular, said body is composed of a container and a cap which is connectible to the same.

BACKGROUND OF THE INVENTION

In the state of the art, bioreactors are commonly known as multi-use or as disposable (single use) systems. Multi-use systems consist of glass and steel and are adapted to be operated together with a control unit. These multi-use systems comprise a glass container and a cap closing the same. By way of this cap, for instance a stirrer, sensors, supply lines and the like are connectible to the interior of the container. As a disadvantage with respect to these multi-use systems, it has been experienced that after the termination of an application, the cleaning of the multi-use systems is sumptuous, time-demanding and, as a consequence, expensive. Additionally, a cleaning method to be used has to be validated first generating further costs. This is an essential fact of all bioreactor applications used on the industrial scale, for example for producing recombinant proteins.

Compared with the multi-use systems for cell culture processes described above, disposable systems are also known. These disposable systems or reactors, respectively, have normally the form of a bag. Such systems are described in EP 1 602 715 B1 and U.S. Pat. No. 6,432,698 B1. During their use, such bags are placed on a swivel table (rocker) and moved back and forth with the same. Compared to the multi-use systems in the stirred tank design described above, these bag reactors produce a smaller cell density than the multi-use reactors described above. In addition, such disposable reactors, which consist of multilayer bags, have the disadvantage that they are not recyclable due to the different plastic materials. For the applicant, these bag-reactors particularly have the disadvantage that conditions of cell culture processes known from glass and steel containers are not directly transferable to bag-reactors. Thus, the applicant has to optimize these bag-reactors for its respective application.

Stirred tank bioreactors are also known as disposable systems. For instance, they comprise a container, stabilised by an inflatable structure according to DE 10 2006 022 651. In US 2005/0239198 and US 2005/0239199, bags placed in a solid casing are used to receive the medium. This casing-bag combination comprises a stirring unit and is composed of disposable objects. The bags are not arbitrarily variable in their sizes since they have to be used in combination with a casing adapted in its size. Further, the flexible bags have a rigid integral adapter for a stirring unit. This construction is complex and expensive to manufacture.

The Superspinner D1000 of Satorius (DF001LS SSB-V) is an alternative construction. This bioreactor is qualified by its rigid walls and its removable cap. The latter has the risk that the bioreactor is opened and contaminated before application or it is opened during use and the contained material is contaminated. Thus, it is not clear for the user whether an actually not opened sterile bioreactor is provided.

It is the objective of the present invention to provide a disposable bioreactor which overcomes the disadvantages described above, has a simplified design compared to the state of the art and can be used efficiently for cell culture processes. It is particularly an object to provide a bioreactor which cannot be arbitrarily opened and closed in order to reduce the risk of contamination.

SUMMARY OF THE INVENTION

Surprisingly, the inventive construction overcomes the disadvantages of known bioreactors. Particularly, the problem of the undesired opening of the bioreactor and, thus, the risk of contamination is prevented. Based on the inventive construction, the user does not have to autoclave for sterilization as well as to prepare the respective documentation for validation. Accordingly, a simplified bioreactor being easy to use is provided for the user.

The above objective is solved by a disposable bioreactor and a cap, forming an essential element of the bioreactor according to the claims. Furthermore, the above objective is solved by a bioreactor system for cell cultivation, a method for the production of the disposable bioreactor and the use of the disposable bioreactor. Further advantageous embodiments and modifications of the present invention will be evident from the following description, the accompanying drawings and the patent claims.

DEFINITIONS

Cell culture process: This term includes all types of aerobic and anaerobic cell cultivation in liquid medium. Particularly, this term includes the cultivation of higher eukaryotic cells (mammal, fish, bird, reptile, amphibian cells, plant cells, algae etc.), lower eukaryotic cells, like fungus (as for example yeasts like *Saccharomyces* sp., *Pichia* sp. and *Kluyveromyces* sp., or filament fungus, like *Aspergillus* sp., *Penicillium*), microorganisms (for example *Lactobacillales* sp., *Actinomyceten*, *Escherichia* sp., *Streptomyces* sp.), infected cells (for example virus infected (for example Baculovirus), bacterial infected) and transformed cells, particularly gene modified microorganisms and cells. The term also covers the cultivation of cells in liquid medium together with carrier materials, as for example pellets, carriers, etc., which can be colonized by cells. This term also includes preparation steps of cell cultivation, as for example the mixing and blending of solutions, suspensions, dispersions, as for example growth medium, wash medium, rinsing medium and buffer etc. Therefore, the bioreactor can be also used as a mixing device.

Body: A body in the meaning of the present invention comprises a closed, fillable inner space which cannot be opened without destruction. Preferably, the body consists of an upper and a lower portion wherein these portions can be formed by only one part or several parts. In a multi-part construction, it is preferred to use a two-part construction in which the upper portion is formed by a cap which cannot be detached from the lower part without destruction. Preferably, the body is connected to the ambiance by means of one or several defined and closable openings by means of which the inner space can be filled, emptied and/or contacted. These one or several openings are situated in the lower and/or upper portion of the body. Preferably, they are arranged in the upper portion wherein they are realized in the cap in two—or multi-part constructions of the body. The openings are configured as connecting cones for tubes, a clamping ring and/or as obstructed openings serving for maintaining and/or positioning of other elements. Preferably, connecting cones are arranged at the upper and lower side of the cap. A clamping ring and/or obstructed openings are arranged preferably only at the upper side of the cap.

Tight: This term describes the property of the body of the bioreactor to be impermeable for water, vapour and/or air at its walls and its edges, particularly in the case of a two- or multi-part body as for example between the outer edge of the cap and the contacting wall of the container. The tightness can be realized by a positive connection of abutting, and mutually contacting walls. Additionally, sealing elements can contribute to the tightness as for example an O-ring, a sealing lip and/or an adhesive. In this case, the sealing element is clamped between the contacting walls of the cap and the container. While assembling a multi-part body, particularly a body formed of a container and a cap, either the sealing element is first arranged on the container and thereafter, the cap is attached or vice versa so that the sealing element is clamped between both parts of the body. Preferably, the sealing element is first attached to the container since this facilitates the assembly. To check the tightness, a so-called pressure test was used by means of which the inner space of the closed body of the bioreactor is pressurized by means of air via a connecting opening with pressure of 1 bar. Before starting the pressure test, all openings and connecting possibilities were closed. According to this pressure test, a bioreactor is tight if the pressure in the closed inner space remains constant at 1 bar for a period of 5 to 10 minutes, preferably 10 to 20 minutes and more preferred 20 to 30 minutes.

Mixer: This term describes elements of the disposable bioreactor, which are connected directly or indirectly to an external driving unit, which are positioned in the inner space of the body of the bioreactor and which realize the mixing of the filled bioreactor. Particularly, the mixing unit is comprised of a magnet, a driving shaft and a mixer. The mixer can be configured differently, particularly it is chosen from the group consisting of an impeller mixer, a propeller mixer, a Rushton mixer and a Pitched-Blade mixer. For an external drive, for example a magnet motor, a particularly adapted accommodation is provided on the disposable bioreactor to realize a detachable connection between the mixer and the drive.

Retaining structure: This term describes an arrangement serving for attachment.

The disposable bioreactor of the present invention comprises a body having rigid walls connected to each other which form and enclose a tillable inner space wherein said rigid walls cannot be detached from each other without destruction and said enclosed inner space can be equipped with at least one disposable bioreactor component, particularly a stirring unit and/or sensor. In a preferred embodiment of the invention, said body is comprised of a container and a cap which cannot be detached from said container without destruction wherein at least one disposable bioreactor component can be arranged at said cap. According to a further embodiment, said cap of said disposable bioreactor comprises the following features: a cap surface with an upper and a lower side, a retaining structure arranged on the lower side of the cap surface with a plurality of locking arms running in the lateral direction, while the locking arms are adapted to be resiliently shortened in the longitudinal direction and to be locked vertically to the longitudinal direction in the container by way of a retaining surface. Besides to this cap, the disposable bioreactor comprises a container with a fixation flange, arranged circumferentially on an opening, which comprises an end portion, bent in the direction of the opening, as a fastening indentation on which the retaining structure of the cap is adapted to be locked. Thus, the container is positively fit by the cap. Further, the cap is realised constructionally such that a mixer unit and at least one sensor can be fixed on the cap and be arranged in the interior of the container.

Due to the special design of its cap, the disposable bioreactor of the present invention combines the advantages of known multi-use and disposable bioreactors. As it is made up of disposable objects, it is also adapted for use as a disposable bioreactor. These inventive disposable bioreactors are shipped in an already closed and sterilised condition. As the rigid wall of the disposable bioreactor's body or preferably the cap cannot be detached from the container of the bioreactor without destruction, the danger of contamination of the bioreactor is minimised. Further, when this disposable bioreactor is used as a disposable system, the expenditure of cleaning as well as the danger of contamination for subsequent utilisation processes is completely avoided.

According to one embodiment of the cap of the present invention, the same features a collar circumferentially arranged on the cap surface and projecting vertically to the cap surface, which is formed resiliently parallel to the cap surface and/or features a circumferential sealing element on its inner side. When the container of the disposable bioreactor is closed by this cap, either the projecting collar bears resiliently against the container, and/or the sealing element is clamped between collar and outer wall of the container. In both alternatives, a tight connection between the container and the cap of the disposable bioreactor is formed.

According to a further embodiment of the cap, the locking arms thereof feature a U-shaped portion on their radially outer end, open in the direction of the cap surface, whose legs are resiliently movable in the longitudinal direction of the locking arms When the cap is set on the container of the disposable bioreactor, at first the legs of the U-shaped portions situated radially on the outer side are resiliently pressed inwardly by the fixation flange of the container. In this way, it is possible to push the retaining structure into the fixation flange in the direction towards the interior of the container. As soon as the retaining structure has been pressed sufficiently deep into the container, the resiliently biased legs of the U-shaped portions snap to the outside again, and engage behind a fastening indentation provided on the fixation flange. Thus, in this position, the locking arms are situated inside the container, and the container is completely closed by the cap surface with the circumferential collar. As a consequence, releasing the locking arms, and thereby this opening of the disposable bioreactor, is only possible by way of destructing the cap. Due to the destruction, the bioreactor cannot be used anymore. In this way it is prevented that the disposable bioreactor is contaminated. Further, this connection between container and cap of the disposable bioreactor promotes that the disposable bioreactor can be provided as being tight so that gas exchange is realized via filter elements arranged in or on said cap.

In a further preferred embodiment of the cap, the retaining structure thereof comprises a centrally arranged bearing flange, in which a driving shaft with impeller and magnet can be rotatably held for driving by a magnet motor. Furthermore, the cap surface features at least one, preferably a plurality of projecting connecting cones as tube connection pieces on the upper and on the lower side thereof, respectively. Preferably at the upper side of the cap, at least one clamping ring is arranged, preferably a plurality thereof, serving for a reliable positioning of elements to be introduced into the bioreactor, as for example probes and sensors. All openings (connecting cones, clamping rings etc.) can be closed either by means of connected elements (tubes, sensors, probes) or by plugs, membranes and/or filters.

With the aid of this cap design, the drive of the stirrer as well as that of the different sensors can take place in a non-invasive manner. For this purpose, the driving shaft with mixer, preferably an impeller, and equipped with a magnet is rotated without contact with the aid of a magnet motor. Furthermore, plastic tubes, preferably silicone tubes, can be fixed on the connecting cones. These plastic tubes are used for instance for arranging sensors within the container. For this purpose, the tubes are closed with a stopper or with a membrane e.g., depending on which kind of sensor is to be placed into the tube. Due to the arrangement of the sensors within the tubes which are fixed on the connecting cones, the same retain their position within the solution in the container. Through this, the disadvantages of the bag reactors (see above) are excluded, in which the sensors frequently reach the surface of the medium in the bag, and measure the air present there instead of the liquid medium.

For the further support of the position of the tubes in the interior of the container, and thus of the position of the sensors, the cap comprises preferably a positioning ring. With the aid of the positioning ring, which is held by way of a central bridge on the driving shaft e.g., the tubes are kept in a distance from each other and are stabilised. This assists in a troubleless operation and use of the sensors inside the container. On the other hand, this positioning ring facilitates the transportation of the sterile and gas-tight bioreactor, namely by stabilising the components which are arranged within the reactor.

It is furthermore preferred to fix the positioning ring described above on the retaining structure by way of a plurality of rods. Furthermore, container and cap as well as said positioning ring of the disposable bioreactor are made of a recyclable material like plastics. Particularly, plastics are preferred which are certified according to United States Pharmacopeia (USP) Class VI. It is also preferred to use reusable plastics for producing the disposable bioreactor which are chosen from the plastics of USP Class VI.

The present invention discloses in addition a disposable bioreactor kit which features the following characteristics: a container with a fixation flange, arranged circumferentially on an opening and comprising an end portion, bent in the direction of the opening, as a fastening indentation, a cap like that which was already described above, whose retaining structure is adapted to be locked on the fastening indentation, a mixer unit and at least one sensor for capturing data of a medium in the container, and instructions for the installation and the use of the disposable bioreactor. In an alternative embodiment, the kit consists of an already closed bioreactor including a mixing unit with connected tubes as well as at least one sensor and instructions for installation and use of the disposable bioreactor. A further embodiment of said kit comprises additionally also the external drive and the control unit by means of which the bioreactor can be operated. Particularly, said sensor is a pH sensor.

Additionally, the present invention discloses a bioreactor system for cell cultivation. This bioreactor system comprises the following features: a disposable bioreactor already described above, a plurality of disposable bioreactor components, particularly a mixing unit and/or a sensor, installed at and/or in said disposable bioreactor, and a control unit by means of which the plurality of disposable bioreactor components can be controlled and/or read out. It is preferred that the control unit comprises a selection of the following components: a main module for control of different cultivation processes, an electric power module for energy supply to the bioreactor system, a driving module for controlling the mixer, a pump module for the controlled supply and/or removal of gases and/or fluids to/from the disposable bioreactor, a heating module for cooling or heating the disposable bioreactor, a pH/DO module and a gas mixing module.

Furthermore, the present invention discloses a method for the production of a disposable bioreactor which features the following steps: 1: producing a one-part body having rigid walls connected to each other which form a fillable inner space and which cannot be detached from each other without destruction, wherein at least one disposable bioreactor component, preferably a stirring unit and/or a sensor is placed in said inner space of said body with. 2: Sterilizing said body. In an alternative embodiment of said method, it is preferred to produce a multi-part body, preferably made of a container and a cap for closing said container. The fillable inner space also includes at least one disposable bioreactor component, particularly a mixing unit and/or a sensor. In this alternative embodiment, first the cap and the disposable bioreactor component, particularly the mixing unit and/or at least one sensor, are connected and in a second step, the cap equipped with said disposable bioreactor component is connected to said container so that a tightly sealed disposable bioreactor is provided. The sealed disposable bioreactor is subsequently sterilized. Preferably, said container is produced with a fixation flange arranged circumferentially on an opening and comprising and end portion, bent in the direction of the opening, as a fastening indentation. Said cap is preferably produced according to the above described construction so that its retaining structure can be locked on the fastening indentation of said container.

Furthermore, the present invention discloses the use of the disposable bioreactor described above and of the disposable bioreactor described above for performing cell culture processes.

DESCRIPTION OF THE ACCOMPANYING DRAWINGS

The present invention is explained in more detail by means of the accompanying drawings.

Figure 2:
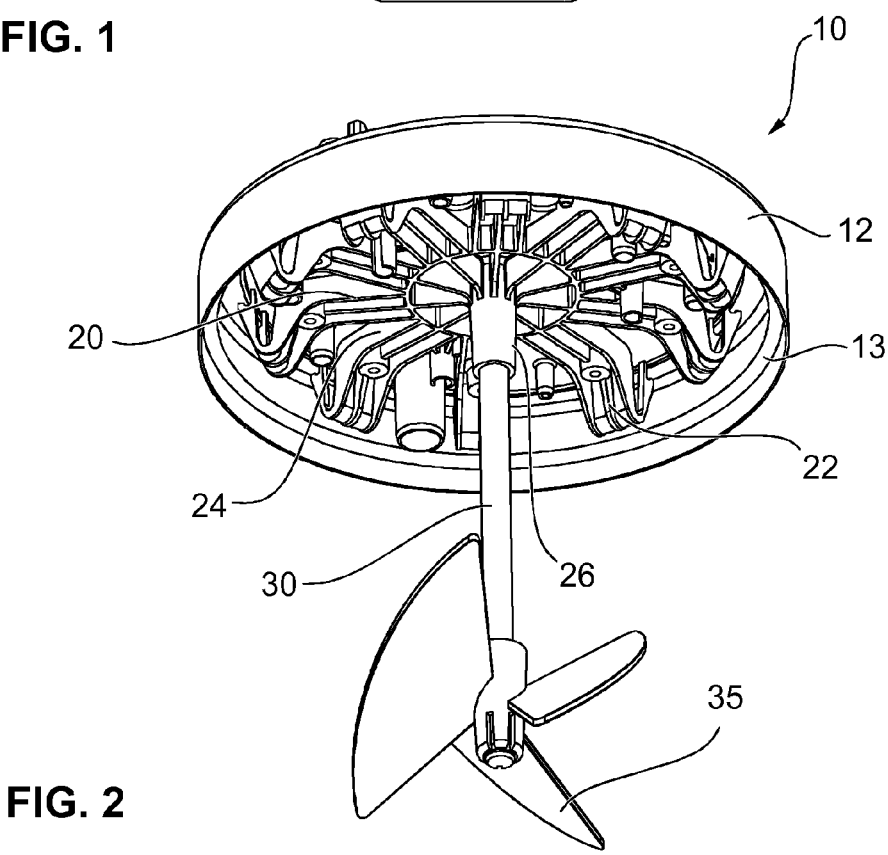
Figure 3:
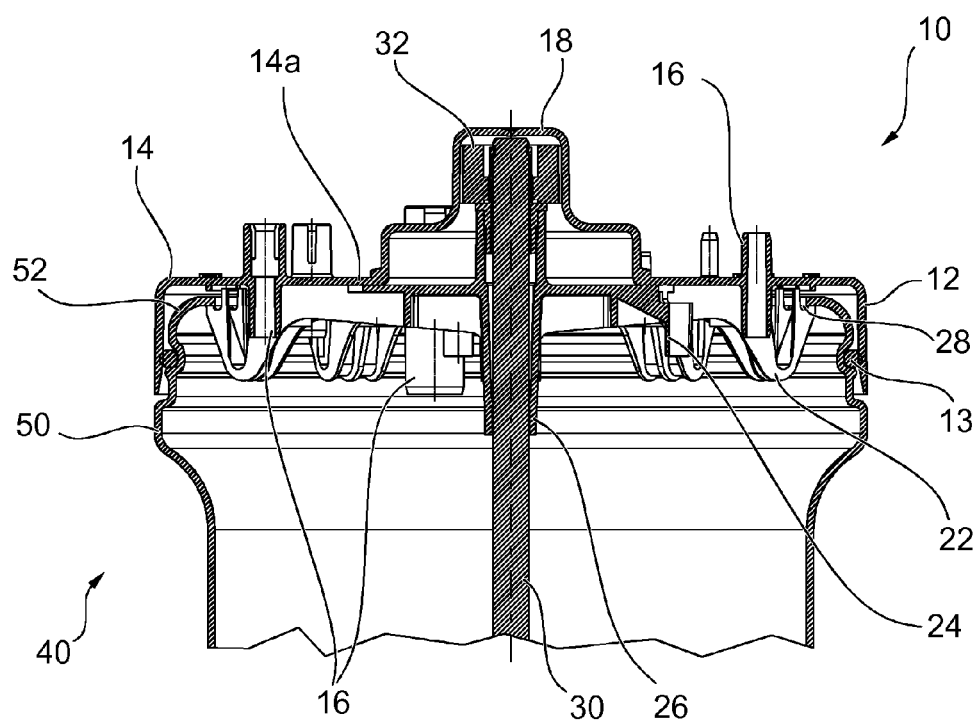
Figure 4:
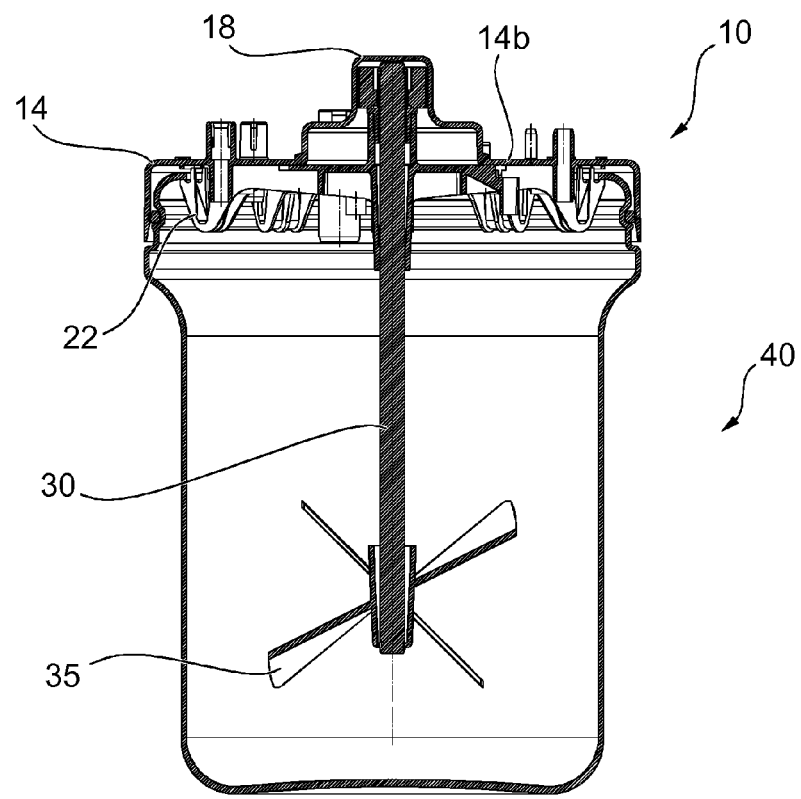
Figure 5:
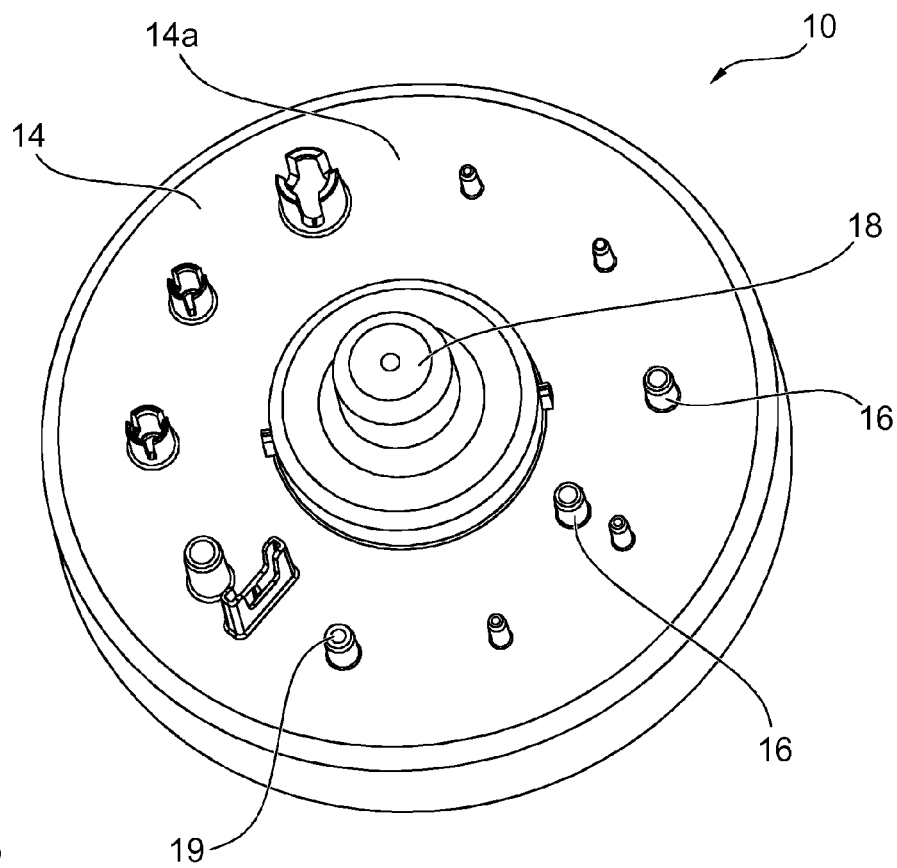
Figure 6:
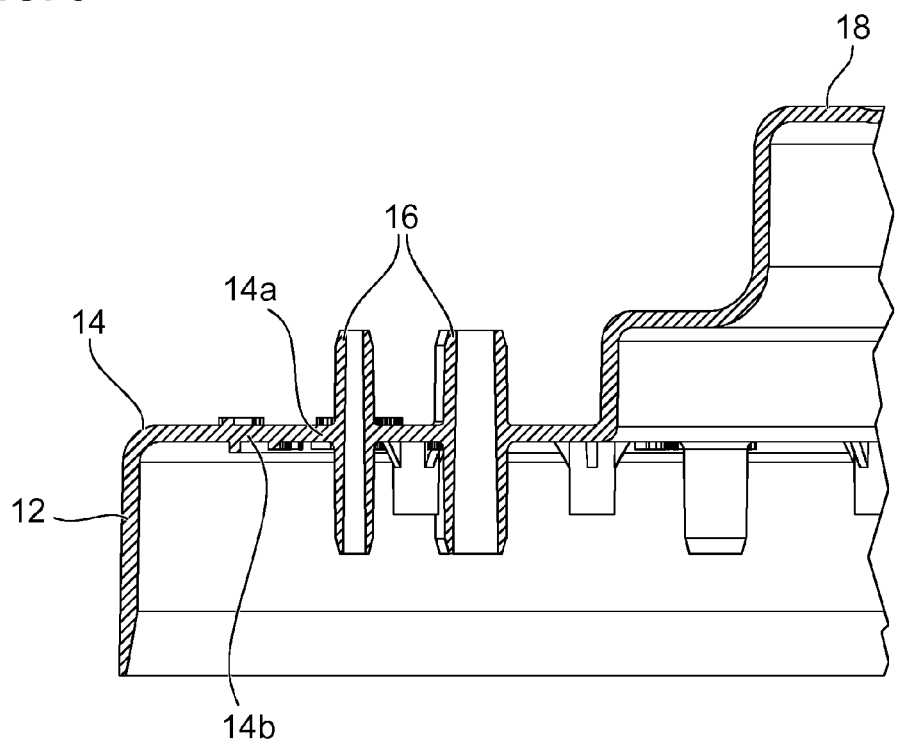
Figure 7:
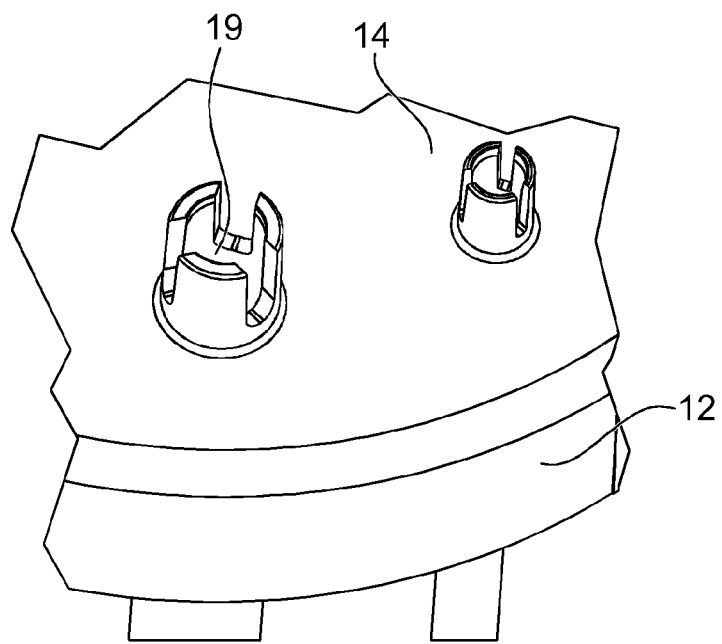
Figure 8:
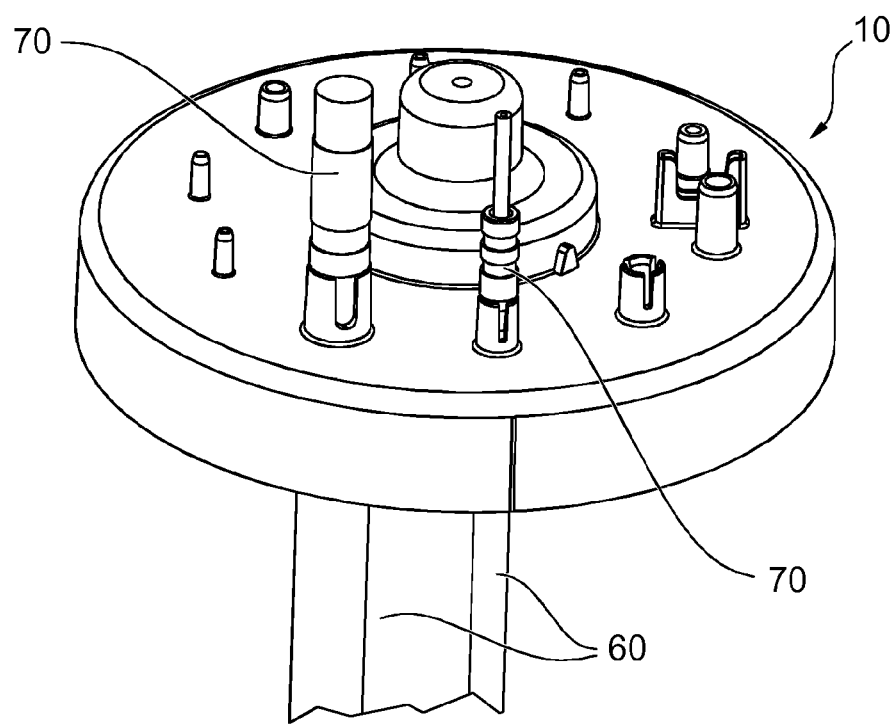
Figure 12:
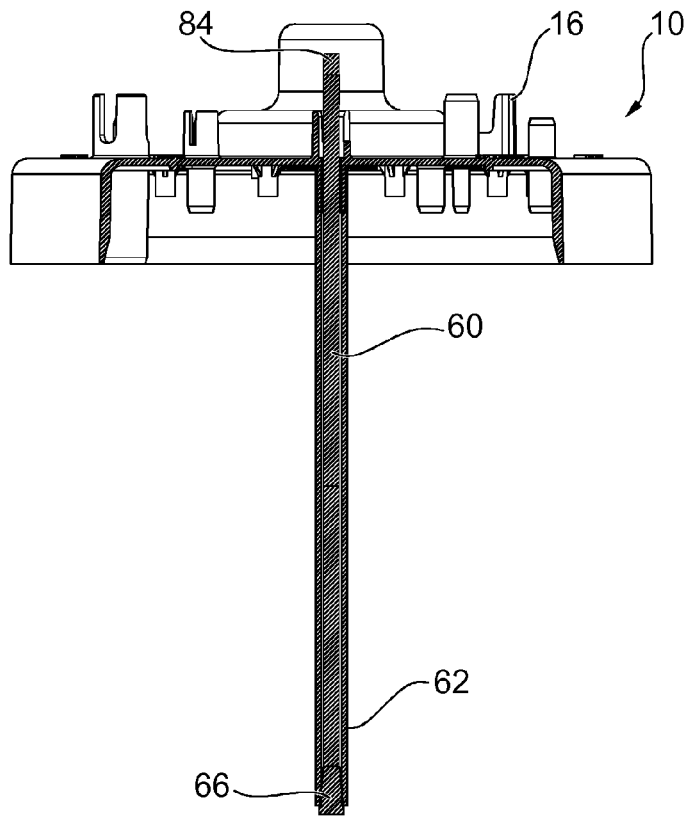
Figure 13:
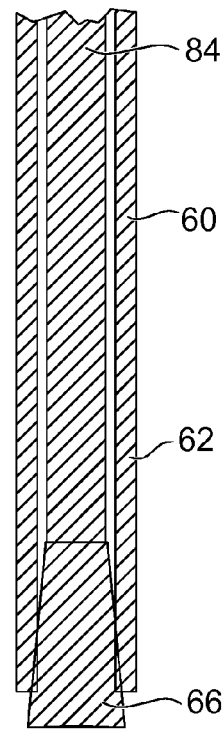
Figure 14:
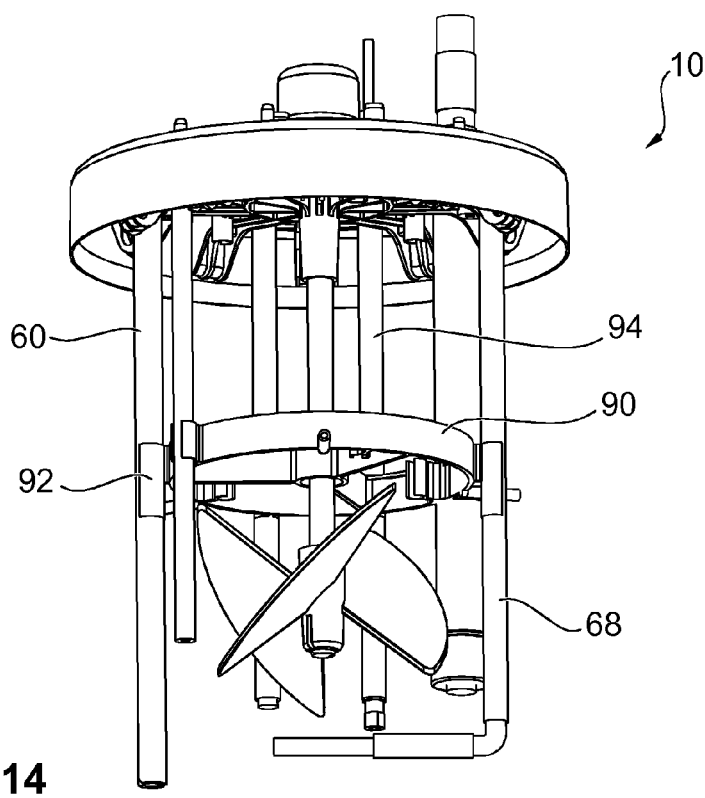
Figure 15:
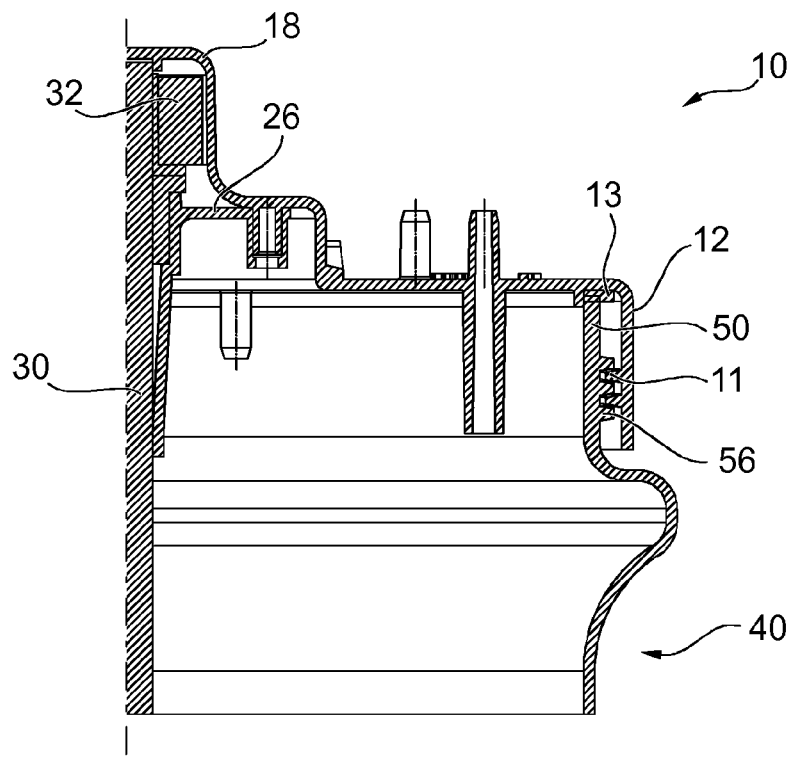
Figure 16:
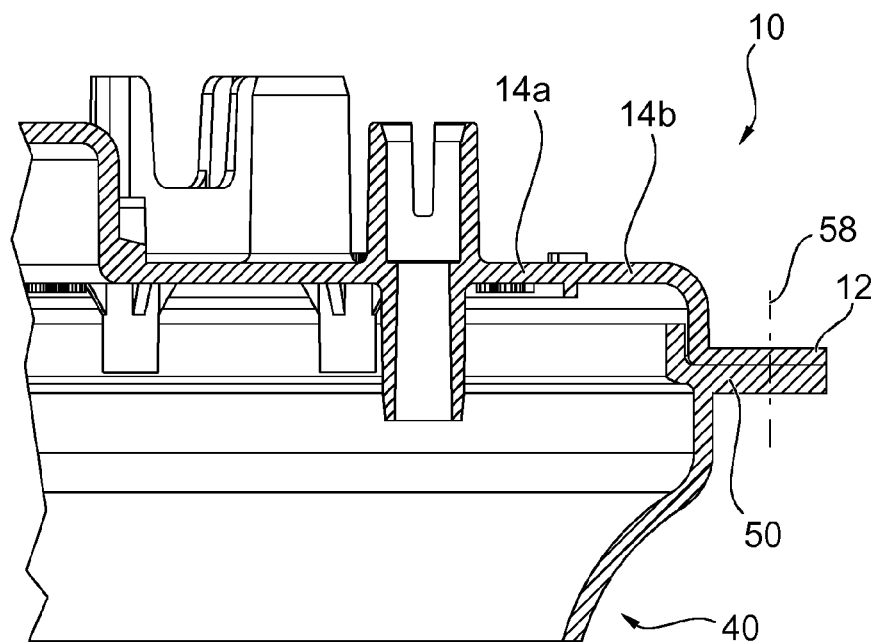
Figure 17:
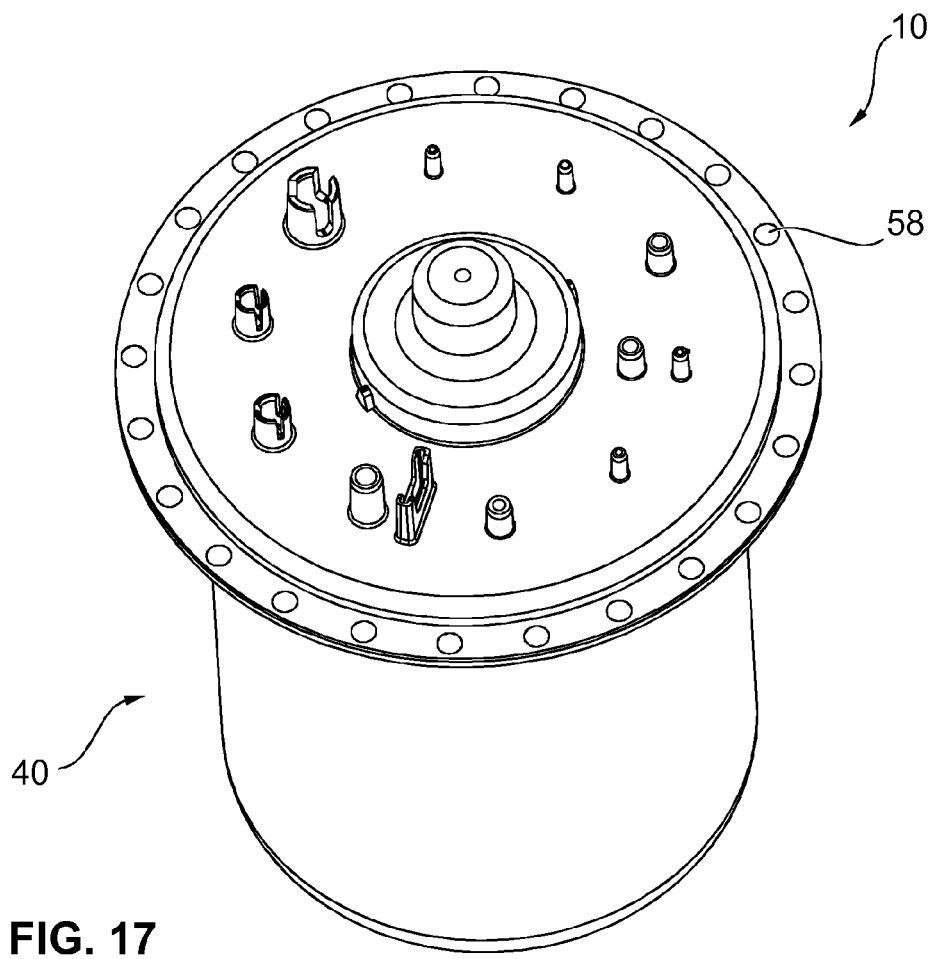
Figure 18:
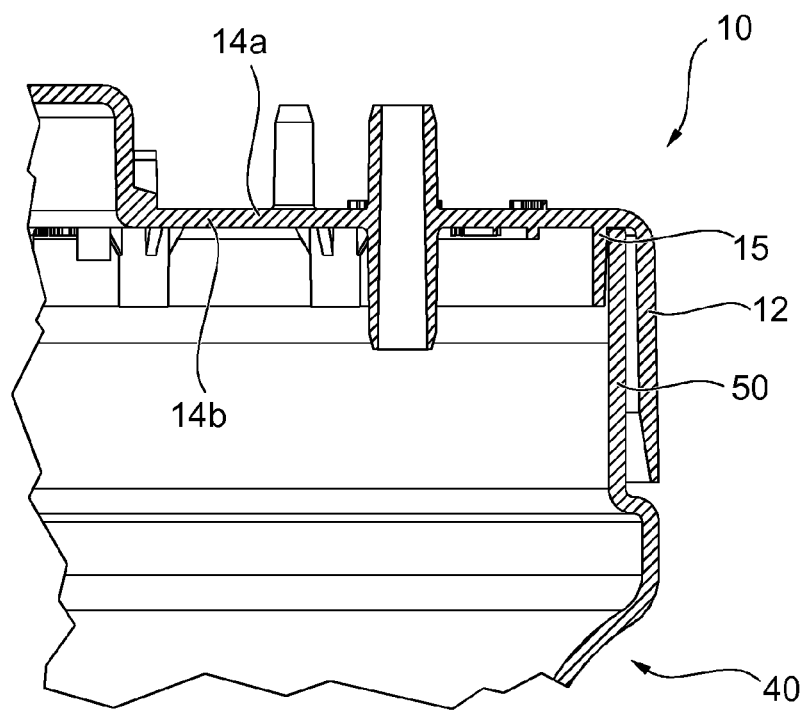

FIG. 1 shows a preferred embodiment of the disposable bioreactor of the present invention, FIG. 2 shows an enlarged view of an embodiment of the cap of the disposable bioreactor with retaining structure, driving shaft and impeller, FIG. 3 shows an enlarged cutout of the cap with retaining structure, installed in the container of the disposable bioreactor, FIG. 4 shows a section view through a part of the disposable bioreactor after FIG. 1, FIG. 5 shows a perspective view of an embodiment of the cap of the disposable bioreactor, FIG. 6 shows a partial section view of the cap from FIG. 5, FIG. 7 shows an enlarged perspective view of a part of the cap from FIG. 5, FIG. 8 shows a perspective view of the cap from FIG. 5 with tube adapters, FIG. 9 shows a section view of the cap from FIG. 5 with an installed tube and sensor, FIG. 10 shows an additional section view of the cap from FIG. 5 with an installed tube and sensor, FIG. 11 shows an enlarged view of the tube end from FIG. 10, situated in the container, FIG. 12 shows a section view of the cap from FIG. 5 with another preferred installed tube with sensor, FIG. 13 shows an enlarged view of the tube end from FIG. 12, FIG. 14 shows a perspective view of a preferred embodiment of the cap with retaining structure, installed tubes and positioning ring, FIG. 15 shows an enlarged sectional view of a preferred connection between the cap and the container, FIG. 16 shows an enlarged sectional view of a further preferred connection between the cap and the container, FIG. 17 shows a perspective plan view of a preferred embodiment of the disposable bioreactor, FIG. 18 shows an enlarged sectional view of a further preferred connection between the cap and the container of the disposable bioreactor.

DESCRIPTION OF THE PREFERRED EMBODIMENT IN DETAIL

The present invention discloses a disposable bioreactor 1, which is described by way of the embodiment according to FIG. 1. Generally, the disposable bioreactor 1 is made of a body 10, 40 consisting of rigid walls connected to each other. These rigid walls connected to each other form and enclose a fillable inner space of said body 10, 40. According to a preferred embodiment described below, said rigid walls connected to each other are provided by a container 40 and a cap 10 connected thereto. The rigid walls connected to each other of said body 10, 40 are not detachable from each other without destruction. This guarantees that the disposable bioreactor is actually used only as a one-way article so that possible following processes are not impeded by for example contamination. Within said inner space of said body, known disposable bioreactor components can be positioned. These disposable bioreactor components include for example a stirring unit and/or a sensor. Said preferred body of the disposable bioreactor is produced for example as a closed one-piece body by means of a blow molding method wherein disposable bioreactor components are already molded into said body. This body comprises preferably a cylindrical shape (not shown) having a bottom platform and a top heading section. In this top heading section, the same connecting features are provided as described below referring to the cap 10 and its preferred embodiments. Based thereon, known disposable bioreactor components can be positioned within said one-piece disposable bioreactor.

Referring to FIG. 1, a preferred embodiment of the disposable bioreactor 1 is comprised of a container 40, which is adapted to be firmly and tight connected to a cap 10, which cannot be detached without destruction. The container 40, the cap 10 as well as other components installed on the bioreactor 1, like tubes 60, positioning aid 90, connection pieces and the like, are made from a plastic material, particularly chosen from plastics certified in USP Class VI. Such plastic materials are commonly known. Since the cap 10 and the container 40 cannot be detached from each other without destruction, they form the above described body having an enclosed inner space.

Due to its construction, the disposable bioreactor 1 provides the advantageous stirred tank design, which can be used without previous cleaning of the system. In this way, the danger of contamination of the bioreactor 1 is diminished, because the disposable bioreactor 1 can be shipped sterile and tight. An air exchange between the inner space of the disposable bioreactor 1 and the environment is realized via at least one filter element (not shown) installed as sterile barrier at said disposable bioreactor 1. Preferably, the at least one filter element is connected directly or indirectly to a connecting cone.

As the disposable bioreactor consists of plastic material, its components container 40, cap 10, retaining structure 20, positioning ring 90, tubes 60 can be produced by conventional forming methods for plastics processing. Therefore, in the frame of the production of the disposable bioreactor, the container 40 is formed first by for instance a blow moulding process. In a further step, the cap 10 and its retaining structure 20 are formed by injection moulding or by a similar method. In a separate method, the inner structure of the bioreactor, particularly the mixing unit, 30, 32, 35 and the position ring 90, are additionally produced. While assembling the whole disposable bioreactor, first the inner structures are attached to the cap 10 by means of screws, glueing and/or welding. Thereafter, the cap 10 equipped with inner structures is mounted on the container 40 by means of screws, glueing and/or welding. Thus, a body 10, 40 is first produced consisting of rigid walls connected to each other. These rigid walls form a fillable inner space and they enclose the same. Furthermore, said rigid walls cannot be detached from each other without destruction as follows for example from the following description of the connection between said cap 10 and said container 40. After the individual components of the disposable bioreactor, as explained in more detail below, were assembled to the disposable bioreactor, it is. Thus, after the completion of the production process, which contains the connection of the container 60 with the cap 10 by way of the retaining structure 20 or alternative constructions as an essential step, a sterilised and gas-tight closed disposable bioreactor is at hand. The constructional details and peculiarities of the individual components of the disposable bioreactor will be explained in the following.

On the cap 10, which will be described in detail below, an external magnet motor M for driving various stirrers 30, 35, tube connection pieces 68 with tubes 60 projecting into the container 60, sensors 82, 84 arranged in the tubes 60, further known components or a selection thereof are connected. The cap 10 is matched to a fixation flange 50 of the container 40. Preferably, the fixation flange 50 is provided together with the container 40 of various dimensions. In this way, the container dimension can be deliberately selected for the individual application of the disposable bioreactor 1, without that special caps 10 must be provided for each container dimension.

As depicted in FIG. 3, the fixation flange 50 is circumferentially arranged on the opening of the container 40. A bent end portion 52 of the fixation flange 50 projects in the direction of the centre point of the opening of the container 40 or of the fixation flange 50. Due to this shaping, the end portion 52 forms a fixation- or locking indentation for the cap 10.

Still preferably, the fastening indentation 52 is provided with a bridge (not shown) projecting in the direction of the bottom of the container 40. This bridge is also formed circumferentially on the opening of the container 40. It assists in a locking of the retaining structure 20 of the cap 10 (see below) on the fastening indentation 52 by forming a positive fit with the retaining arms 24 of the retaining structure 20, which engage there.

The cap 10 is shown in a perspective view in FIGS. 2 and 5. It comprises a cap surface 14 with a lower side 14b facing the container 40 and an upper side 14a turned away from the container 40. In the shown embodiment, the cap surface is executed to be round, whereas angular, oblong or curvilinear forms are also conceivable.

The cap surface 14 is limited by a circumferential collar 12, projecting vertically with respect to the cap surface 14. The collar 12 projects in the direction of the container 40 in order to surround the fixation flange 50 when the container 40 is being closed. According to one embodiment, the collar is executed resiliently in the radial direction. Furthermore, it is executed somewhat smaller in its inner diameter than the outer diameter of the fixation flange 50. After fastening the cap 10 on the container 40, the collar 12 and the fixation flange 50 bear against each other and form a tight connection.

According to a further embodiment, the collar 12 comprises a sealing element 13 on its radial inner side. The sealing element 13 projects radially inwardly in the direction of the fixation flange 50. It is formed by a flexible sealing lip or an O-ring 13, for instance. When the cap 10 is fastened on the container 40, the sealing element is clamped in between the collar 12 and the fixation flange 50. In this way, a tight connection between the container 40 and the cap 10 is produced. In an alternative embodiment, the container 40 comprises a sealing element 13. It is arranged onto the radial outer side of the fixation flange 50. The sealing element 13 is preferably realised by an O-ring or a sealing lip. According to an embodiment, it is arranged in a circumferential groove or nut and it projects radially outwardly in the direction of the collar 12 of the cap 10. While attaching the cap 10 at the container 40, the sealing element 13 is clamped between the fixation flange 50 and the collar 12. In this manner, a tight connection is realized between the container 40 and the cap 10. This embodiment is preferred since it simplifies the assembly of the disposable bioreactor.

The retaining structure 20 is fastened on the lower side 14b of the cap surface 14. This fastening can be produced by means of welding, screwing and/or glueing. The retaining structure 20 serves for locking the cap 10 on the container 40, so that the cap 10 can no more be detached from the container 40 without destruction. Whereas the retaining structure 20 is executed as a star-like structure for a circular cap 10 in the present preferred embodiment, other forms matched to the shape of the cap are also conceivable. In this, the function of the retaining structure 20 must be fulfilled, namely to be lockable on the fixation flange 50 of the container 40 such that it is not detachable from the outside.

The retaining structure 20 comprises a centrally arranged bearing flange 26. The bearing flange 26 holds the driving shaft 30 with impeller 35. Preferably, the impeller 35 is frictionally fitting on the driving shaft 30 with the aid of a setup sleeve. On the end of the driving shaft 30, turned away from the impeller, a driving magnet 32 is fastened on the driving shaft 30. This magnet 32, and with it also the driving shaft 30, are rotatable without contact by way of the magnet motor M. Parts of the bearing flange 20 as well as the driving magnet 32 are held in a dome-shaped accommodation 18 of the cap 10, preferably the bearing flange 26 is screwed into the dome-shaped accommodation 18. This dome-shaped accommodation 18 serves also for the fixation of the magnet motor M.

A plurality of locking arms 24 extend in the lateral direction from the bearing flange 26, i.e., in the direction of the collar 12. The locking arms 24 are made of a stable plastic material, in order to be adapted to lock the cap 10 durably on the container 40. For realising this locking, the locking arms 24 are adapted to be resiliently shortened in their longitudinal direction. For this purpose, the locking arms 24 have a U-shaped portion 22 on their ends facing the collar 12, which is open in the direction of the cap surface 14. The legs of this U-shaped portion 22 are resiliently movable in the longitudinal direction of the locking arms 24. The lateral or radial extension of the retaining structure 20 with the locking arms 24 and the U-shaped portions 22 is greater than the inner diameter of the fixation flange 50 of the container 40. When the cap 10 is fastened on the container 40 by pressing the cap 10 in the direction of the container bottom, the legs of the U-shaped portions 22 are moved radially inwardly by the fixation flange 50. Through this, the locking arms 24 are shortened in their longitudinal direction and the radially outer leg of the U-shaped portion 22 is resiliently biased against the fixation flange 50. As soon as the locking surface 28 of the U-shaped portion 22 is arranged below the fastening indentation 52 in the form of a shoulder, the U-shaped portion 22 returns into its initial shape. Through this, the locking arms 24 recover their initial length and lock themselves on the fastening indentation 52 or engage behind it, respectively. The locking surface 28 is differently configured according to different embodiments of the present invention. According to a first alternative (not shown), the locking surface 28 is plane so that it abuts nearly completely at the lower side 14b of the cap 10. According to a second alternative (not shown), the locking surface 28 is configured U-shaped so that it forms a positive connection with a circumferentially arranged rip at the fixation flange 50 (see above). According to a third alternative, the locking surface 28 is U-shaped having U-legs of different length. Referring to the locking arm 24, the radially inwardly positioned U-leg of the locking surface 28 is longer than the radially outwardly positioned U-leg (see FIG. 3). Based on this shape, the U-shaped portion 22 of the locking arm 24 elastically moves in a radial outward direction in limited manner if the retaining structure 20 latches at the fixation flange 50.

In order to assist in the locking between the container 40 and the cap 10, the bridge 54 on the fastening indentation 52 and a retaining surface 28, formed complementary to it on the front surface of the radially outer leg of the U-shaped portion 22, constitute a positive fit.

FIGS. 3 and 4 show the cap 10 in a connection to the container 40, which cannot be detached without destruction. The U-shaped portions 22 are locked below the fastening indentation 52. In addition, they are completely covered up against the outer side of the disposable bioreactor 1 through the cap surface 14 and the collar 12. As a consequence, detaching the cap 10 from the container 40 is no more possible without destruction. Furthermore, one recognises in FIG. 4 the installed driving shaft 30 with impeller 35. The impeller 35 shown here by way of example can have the shapes of quite different stirrers, like that of a Rushton stirrer, a pitched blade stirrer or a propeller stirrer e.g.

According to FIGS. 5 to 7, the cap surface 14 comprises a plurality of openings, as clamping rings 19 and connecting cones 16, which either project on its upper 14a and/or lower side 14b. The connecting cones 16 on the upper side are for the fixation of tubes and adapters 70. The connecting cones 16 on the lower side are for the fixation of tubes 60 for supplying and discharging media or for the arrangement of sensors 82, 84. Depending on the use of the connecting cones 16 and tubes 60, as well as of the installed sensors 82, 84, 86, the same have diameters of different dimensions. This is illustrated in the sectional view of FIG. 6.

Furthermore, the upper side of the cap surface 14 features a plurality of resilient clamping rings 19. The same consist of a plurality, preferably three, resiliently arranged tongues or bridges. Like the connecting cones 16, the clamping rings 19 are preferably produced with diameters of different dimensions. The clamping rings 19 serve for the accommodation and for holding by frictional fit of coupling adapters 70 for the sensors 82, 84, 86 which are to be put into the container 40, or for similar supplementary components of the disposable bioreactor 1.

The tubes 60 arranged in the container 40 are put onto the connecting cones 16 on the lower side of the cap surface 14 and are held by way of frictional fit. In order to keep the tubes 60 and the sensors arranged thereon in their positions within the container 40, the tubes 60 are stabilised and supported by way of a positioning ring 90. As shown in FIG. 14, the positioning ring 90 features circumferentially arranged clamps, on which the tubes 60 are fastened. Within the positioning ring 90, there is an aligning ring, which encompasses the driving shaft 30 and is connected to the positioning ring 90 by way of bridges. Preferably, the positioning ring 90 is held by way of rods 94. On one end, the rods 94 are fixed on the lower side of the cap surface 14 or on the retaining structure 20. On their other end, the rods 94 are held on the radially inner side of the positioning ring 90. Due to this, the positioning ring 90 can be fixedly arranged in the inner space of the container 40, so that not only the position of the tubes 60 and of the sensors is assured, but also a transportation lock is provided for the disposable bioreactor 1.

Via the connecting cones 16, different components are arranged in the interior of the container 40. According to one embodiment, a tube 68 is provided in the interior of the container 40, which has an angled elbow piece near to the bottom of the container 40. For this reason, the end of the tube 68 runs parallel to the bottom of the container 40. It is closed by a porous filter. This filter serves for the aeration of the medium in the container 40.

According to a further embodiment shown in FIG. 12, a temperature sensor 84 is arranged in the container 40. The temperature sensor 84 is located in a tube 60, which is closed by a stopper 66 at its end 62. The temperature sensor 84 is put into the container 40 via the cap 10. The temperature transition takes place via the tube 60. The temperature change during a cell culture process is so small that the response time of the measurement through the wall of said tube 60 can be neglected.

A DO-sensor (Dissolved Oxygen sensor) 82 is inserted within a tube 60 having a silicone cap 64 (compare FIGS. 10 and 11). The cross section of the DO sensor 82 is matched to one of the connecting cones 16, such that a frictionally fitting connection between the connecting cone 16 and the DO sensor 82 results. On this basis, the sensor can be arbitrarily positioned in the tube 60, without having to use an additional adapter. Preferably, this sensor is positioned in such a way that it is moved until the end of the tube.

According to the embodiment in FIG. 9, a pH-sensor 86 is installed in the container 40. For this purpose, a tube 60, preferably a silicone tube as used with the other sensors, is fastened on a connecting cone 16 on the lower side 14b of the cap surface 14. In front of this connecting cone 16, a clamping ring 19 is arranged on the upper side 14a of the cap surface 14. A coupling adapter 70 for the pH-sensor 86 is held within the clamping ring 19 by frictional fit. Within the tube 60 extends a rigidly formed or stiffened optical guide of the pH-sensor 86. At the end 62 of the tube 60, there is a pH-sensor adapter 88 with a light-sensitive spot 89 on its axial front side. Said rigidly formed optical guide/fibre of the pH-sensor 86 ends adjacent to said light-sensitive spot 89 of said adapter 88 within said tube 60. Based on the rigid construction of said optical guide, it is guaranteed that the distance between the end of the optical guide and the light-sensitive spot 89 remains constant during use of the disposable bioreactor 1. Thereby, a reliable measuring by said pH-sensor 86 is supported. During use, the light-sensitive spot 89 is first stimulated by said optical guide of said pH-sensor 86 and thereafter, its emission of light is sensed by the optical guide of said pH-sensor 86.

While the disposable bioreactor has been described as an entity above, the present invention provides also a bioreactor kit, a kit for a disposable bioreactor in particular. This kit comprises the container 40 described above, the cap 10, the mixer unit 30, 32, 35, tubes as well as a selection of the sensors described above, which are adapted to be installed in the container 40 or on the cap 10, respectively. The described components of the disposable bioreactor are provided as individual components in the kit. This provides the possibility to assemble it, to sterilise the disposable bioreactor on location and to use it for an utilisation which is aimed at. The steps necessary for this are contained in the instructions for installation and use, which are also contained in the bioreactor kit. Further, this bioreactor kit provides the possibility that containers 60 of different dimensions, but with identical fixation flange 50 are shippable, in order to be able to combine them with the cap 10 and its retaining structure 20 according to the requirements. In an alternative embodiment, the kit consists of the closed disposable bioreactor including the mixing unit and connected tube as well as at least one sensor and instructions for installation and use of the disposable bioreactor. In a further embodiment, said kit comprises additionally an external drive and the control unit by means of which the bioreactor is operated.

After the disposable bioreactor has been delivered from stock in a completely assembled condition, this disposable bioreactor is ready to be used for cell culture processes. The same applies after the assembling of the individual components of the disposable bioreactor kit to a complete disposable bioreactor.

FIGS. 15 to 18 show further preferred embodiments of said cap 10 and said container 40 of the disposable bioreactor 1 as well as their connection to each other. According to the embodiment as shown in FIG. 15, the fixation flange of the container 40 is cylindrically formed. At its radial outer side, a thread 56 is formed. At the upper side of the fixation flange 50, a sealing element 13 is arranged. The cap 10 also comprises a thread 11 at the radial inner side of its collar 12. This thread 11 matches to the thread 56 of the fixation flange 50. By means of the threads 11, 56 complementary shaped to each other, the cap 10 is screwed onto the fixation flange 50 of the container 40. If the cap 10 is completely screwed onto the fixation flange 50, the sealing element 13 is compressed between the lower side 14b of the cap 10 and the upper face of the fixation flange 50 so that the inner space of the disposable bioreactor 1 is tightly closed. In said embodiment of the cap 10, no retaining structure 20 is provided. In the middle of said cap 10, the bearing flange 26 is arranged below said accommodation 18 for the magnet motor for retaining the driving shaft 30 with magnet 32.

Referring to the illustration of FIG. 15, it is also preferred to form the engaging threads 11, 56 as a locking or latching connection between said collar 12 and said fixation flange 50. In such an embodiment, said collar 12 comprises at least one latching rip 11 engaging to at least one latching groove 56 of said fixation flange 50 as soon as said cap 10 is mounted on said container 40. The inner space of the disposable bioreactor 1 is sealed by means of said sealing element 13. It is also preferred to realize the connection between the latching rip 11 and the latching groove 56 as a labyrinth seal. Said labyrinth seal can be used alone or in combination with said sealing element 13.

A further preferred embodiment for mounting said cap 10 on said container 40 is shown in FIG. 16. In this embodiment, the collar 12 and the fixation flange 50 comprise radially projecting and circumferentially extending webs. These webs 12, 50 abut each other. Also in this embodiment, no retaining structure 20 is provided at said cap 10. Said webs 12, 50 abutting each other are permanently connected to each other by means of for example vibration or ultrasonic welding. According to a further preferred embodiment, said webs 12, 50 are connected by means of connecting elements 58 (only schematically shown). For this application, screws, rivets and the like are suitable connecting elements 58. It is also preferred to combine the screwing or riveting of said cap 10 and said container 40 with a glueing of the webs 12 and 50. As a further alternative, said glueing of said webs 12, 50 can be used without any connecting element 58. FIG. 17 shows a perspective view of a cap 10 connected to the container 40 by means of connecting elements 58.

FIG. 18 provides a further preferred embodiment of the connection between the cap 10 and the container 40 of the disposable bioreactor 1. In this embodiment, the fixation flange 50 is cylindrically shaped. Said fixation flange 50 engaging a glueing recess of said cap 10 provided between said collar 12 and a web 15 extending in parallel arrangement to said collar 12. If, for example, said glueing recess between said web 15 and said collar 12 is filled by an adhesive, said fixation flange 50 is rigidly and permanently mounted on the one hand and, on the other hand, a tight connection is realized between said cap 10 and said container 40.

The different above described embodiments of the disposable bioreactor 1 are used within a bioreactor system for cell cultivation. This bioreactor system is qualified by a high flexibility in its application to different cell types since it consists of different modular components. Dependent on the application, the modular components can be combined with a control unit and said disposable bioreactor 1. The disposable bioreactor 1 is equipped with a selection of the already above described disposable bioreactor components. They include for example the mixer, different sensors, supply and removable tubes and filter elements. The control unit by means of which the plurality of disposable bioreactor components can be controlled and/or read out comprises at least a main module for controlling the cell cultivation processes of different cell types. The main module can be optionally combined with different further modules dependent on the disposable bioreactor components connected to said disposable bioreactor and on the application to be processed by said bioreactor system. These further modules comprise an electric supply module for power supply to the bioreactor system, a driving module for controlling the mixer, a pump module for the controlled supply and/or removal of gases and/or liquids to/from said disposable bioreactor, a heating module for cooling or heating the disposable bioreactor, a pH/DO module for controlling the pH value and/or the DO value of the medium in said disposable bioreactor and a gas mixing module for controlling the gas composition in said disposable bioreactor as well as the supply and/or the removal of gases to and/or from said disposable bioreactor.

PARTS LIST 1 bioreactor
10 cap
11 thread; latching connection
12 collar
13 O-ring, sealing element
14 cap surface
14a uppers side of the cap
14b lower side of the cap
15 web
16 connecting cone
18 accommodation for magnet motor
19 clamping ring
20 retaining structure
22 U-shaped portion
24 locking arm
26 bearing flange
28 locking surface
30 driving shaft
32 magnet
35 impeller
40 container
50 fixation flange
52 end portion
56 thread, latching connection
58 connecting element
60 tube
62 tube end
64 membrane
66 stopper
68 tube
70 tube adapter
82 DO-sensor
84 temperature sensor
86 coupling of the pH sensors
88 pH-sensor adapter
89 light-sensitive spot
90 positioning ring
92 fixation element
94 rods
M drive

The invention claimed is:

1. A cap of a disposable bioreactor which is connectible to a container, said cap comprising a cap surface having an upper side and a lower side, said cap surface being limited by a circumferential collar projecting vertically relative to said lower side and attached to surround a fixation flange of the container, said lower side being provided with locking arms which coact with a corresponding fastening indentation of the container, wherein the fixation flange of the container has a bent end portion in the direction of an opening of the container forming the fastening indentation, the locking arms extending in a lateral direction from a bearing flange of the cap in the direction of the circumferential collar, said locking arms being resiliently shortable in their longitudinal direction in which the lateral extension of the locking arms is greater than the inner diameter of the fixation flange or the bent end portion, respectively, and the locking arms are adapted to engage the bent end portion of the fixation flange by way of a retaining surface.

2. A cap according to claim 1, wherein said locking arms each have a U-shaped portion on a radially outer end, open in the direction of the cap surface, said U-shaped portion defining legs that are resiliently movable in the longitudinal direction of the locking arms.

3. A cap according to claim 1, wherein said cap surface is circularly formed.

4. A cap according to claim 1, further including a retaining structure comprising a centrally arranged bearing flange, in which a driving shaft with a mixer can be rotatably held for driving by a magnet motor.

5. A cap according to claim 1, wherein said cap surface features a plurality of projecting connecting cones as tube connection pieces on at least one of the upper and the lower side thereof.

6. A cap according to claim 1, wherein said cap surface features at least one resilient clamping ring as a connection piece, with an adjoining passage opening to the lower side of the cap surface.

7. A cap according to claim 5, wherein said connecting cones on the lower side of the cap surface are connected to a plurality of tubes by means of frictional fit, in which a sensor can be positioned and which can be closed by way of at least one of a stopper, a membrane and via which a medium can be supplied or discharged.

8. A cap according to claim 7, further comprising a positioning ring, by which the tubes are kept in a distance from each other and are stabilized.

9. A cap according to claim 8, wherein said positioning ring is fixed on the retaining structure by way of a plurality of rods.

10. A cap according to claim 4, wherein said retaining structure is fixed on the cap surface by means of at least one of screwing, welding and gluing.

11. A cap according to claim 1, wherein said circumferential collar has a circumferential sealing element on an inner side thereof.

12. A cap according to claim 4, wherein said driving shaft with a mixer includes an impeller and magnet that can be rotatably held for driving by said magnet motor.

* * * * *